US010589090B2

(12) United States Patent
Feldman et al.

(10) Patent No.: US 10,589,090 B2
(45) Date of Patent: Mar. 17, 2020

(54) IMPLANTABLE STIMULATOR DEVICE WITH MAGNETIC FIELD SENSING CIRCUIT

(71) Applicant: Boston Scientific Neuromodulation Corporation, Valencia, CA (US)

(72) Inventors: Emanuel Feldman, Simi Valley, CA (US); Goran N. Marnfeldt, Valencia, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 171 days.

(21) Appl. No.: 15/695,942

(22) Filed: Sep. 5, 2017

(65) Prior Publication Data
US 2018/0071522 A1 Mar. 15, 2018

Related U.S. Application Data

(60) Provisional application No. 62/393,008, filed on Sep. 10, 2016.

(51) Int. Cl.
*A61N 1/08* (2006.01)
*A61N 1/37* (2006.01)
*A61N 1/05* (2006.01)
*A61N 1/378* (2006.01)
*G01R 33/02* (2006.01)
(Continued)

(52) U.S. Cl.
CPC ............ *A61N 1/086* (2017.08); *A61N 1/05* (2013.01); *A61N 1/378* (2013.01); *A61N 1/3718* (2013.01); *G01R 33/02* (2013.01); *G01R 33/285* (2013.01); *H02M 3/155* (2013.01); *H03K 7/08* (2013.01);
(Continued)

(58) Field of Classification Search
CPC ........ A61N 1/05; A61N 1/086; A61N 1/3718; A61N 1/378; A61B 2017/0003; H01F 17/04
See application file for complete search history.

(56) References Cited

U.S. PATENT DOCUMENTS 5,280,239 A * 1/1994 Klimovitsky .......... G01B 7/003
324/207.17
5,287,059 A * 2/1994 Ando ..................... G01N 27/82
324/253

(Continued)

OTHER PUBLICATIONS

International Search Report and Written Opinion regarding corresponding PCT application No. PCT/US2017/050311, dated Nov. 7, 2017.

*Primary Examiner* — Christopher A Flory
(74) *Attorney, Agent, or Firm* — Lewis & Reese, PLLC

(57) ABSTRACT

An implantable pulse generator (IPG) for an implantable medical device is disclosed herein. The IPG is capable of sensing the presence of an external magnetic field, such as a magnetic field associated with magnetic resonance imaging (MRI). The IPG includes a circuit that contains a magnetic core inductor and that is configured to boost a first voltage to a second voltage and use the second voltage to drive a current through a load. In a strong magnetic field, the magnetic core of the inductor becomes magnetically saturated, causing the inductance of the inductor to sharply drop. The inductance drop can be detected, for example, by detecting an increase in the second voltage. The circuit may be a boost converter circuit used to provide a compliance voltage for operation of the IPG.

16 Claims, 9 Drawing Sheets

(51) Int. Cl.
  *G01R 33/28* (2006.01)
  *H02M 3/155* (2006.01)
  *H03K 7/08* (2006.01)
  *A61B 17/00* (2006.01)
  *H01F 17/04* (2006.01)

(52) U.S. Cl.
  CPC ............... *A61B 2017/0003* (2013.01); *A61B 2017/00039* (2013.01); *H01F 17/04* (2013.01)

(56) References Cited

U.S. PATENT DOCUMENTS

| | | | |
|---|---|---|---|
| 6,181,969 B1 | 1/2001 | Gord | |
| 6,516,227 B1 | 2/2003 | Meadows et al. | |
| 6,553,263 B1 | 4/2003 | Meadows et al. | |
| 7,127,298 B1 | 10/2006 | He et al. | |
| 7,177,698 B2 | 2/2007 | Klosterman et al. | |
| 7,444,181 B2 | 10/2008 | Shi et al. | |
| 7,539,538 B2 | 5/2009 | Parramon et al. | |
| 7,623,916 B2 | 11/2009 | Julian | |
| 7,801,600 B1 | 9/2010 | Carbunaru et al. | |
| 7,801,602 B2 | 9/2010 | McClure et al. | |
| 7,872,884 B2 | 1/2011 | Parramon et al. | |
| 7,881,803 B2 | 2/2011 | Parramon et al. | |
| 7,890,182 B2 | 2/2011 | Parramon et al. | |
| 8,606,362 B2 | 12/2013 | He et al. | |
| 8,620,436 B2 | 12/2013 | Parramon et al. | |
| 8,649,858 B2 | 2/2014 | Griffith et al. | |
| 8,768,453 B2 | 7/2014 | Parramon et al. | |
| 9,002,465 B2 | 4/2015 | Ranu | |
| 9,008,790 B2 | 4/2015 | Griffith et al. | |
| 9,037,241 B2 | 5/2015 | Lamont et al. | |
| 9,061,140 B2 | 6/2015 | Shi et al. | |
| 9,174,051 B2 * | 11/2015 | Marnfeldt | A61N 1/36125 |
| 9,220,901 B2 * | 12/2015 | Gururaj | A61N 1/36142 |
| 9,233,254 B2 * | 1/2016 | Nimmagadda | A61N 1/378 |
| 9,259,574 B2 | 2/2016 | Aghassian et al. | |
| 9,308,373 B2 | 4/2016 | Lee | |
| 9,314,632 B2 | 4/2016 | Marnfeldt et al. | |
| 9,327,135 B2 | 5/2016 | Vansickle et al. | |
| 9,352,162 B2 | 5/2016 | Lamont et al. | |
| 9,397,639 B2 | 7/2016 | Feldman et al. | |
| 2006/0173493 A1 | 8/2006 | Armstrong et al. | |
| 2007/0191914 A1 | 8/2007 | Stessman | |
| 2008/0071168 A1 * | 3/2008 | Gauglitz | A61N 1/3718 600/423 |
| 2009/0182389 A1 * | 7/2009 | Stessman | A61N 1/3718 607/11 |
| 2010/0268309 A1 | 10/2010 | Parramon et al. | |
| 2011/0160565 A1 * | 6/2011 | Stubbs | A61N 1/37 600/411 |
| 2011/0160806 A1 * | 6/2011 | Lyden | A61N 1/08 607/63 |
| 2011/0306860 A1 * | 12/2011 | Halperin | A61N 1/05 600/372 |
| 2012/0046707 A1 * | 2/2012 | Gauglitz | A61N 1/3718 607/6 |
| 2012/0053652 A1 * | 3/2012 | Dianaty | A61N 1/08 607/30 |
| 2012/0095529 A1 | 4/2012 | Parramon et al. | |
| 2012/0215271 A1 * | 8/2012 | Min | A61N 1/3718 607/6 |
| 2012/0277817 A1 | 11/2012 | Ellingson et al. | |
| 2013/0184794 A1 | 7/2013 | Feldman et al. | |
| 2013/0245723 A1 * | 9/2013 | Gururaj | A61N 1/36142 607/62 |
| 2013/0289638 A1 * | 10/2013 | Newman | A61N 1/08 607/6 |
| 2013/0325085 A1 | 12/2013 | Carbunaru et al. | |
| 2014/0194729 A1 * | 7/2014 | Gauglitz | A61N 1/3718 600/417 |
| 2015/0134029 A1 * | 5/2015 | Ozawa | A61N 1/36125 607/60 |
| 2015/0144183 A1 | 5/2015 | Yang et al. | |
| 2015/0157861 A1 | 6/2015 | Aghassian | |
| 2016/0051825 A1 | 2/2016 | Ter-Petrosyan et al. | |
| 2017/0173328 A1 * | 6/2017 | Ostroff | A61N 1/3756 |

\* cited by examiner

| Magnetic Field (T) | Inductor A Inductance (µH) | Inductor B Inductance (µH) |
|---|---|---|
| 0.0 | 49.3 | 43.5 |
| 0.2 | 1.2 | 1.7 |
| 0.4 | 0.85 | 0.9 |
| 0.6 | 0.73 | 0.74 |
| 0.8 | 0.66 | 0.72 |
| 1.0 | 0.52 | 0.63 |
| 1.3 | 0.60 | 0.76 |

IMPLANTABLE STIMULATOR DEVICE WITH MAGNETIC FIELD SENSING CIRCUIT

CROSS REFERENCE TO RELATED APPLICATIONS

This is a non-provisional application based on U.S. Provisional Patent Application Ser. No. 62/393,008, filed Sep. 10, 2016, which is incorporated by reference in its entirety, and to which priority is claimed.

FIELD OF THE INVENTION

The present invention relates to an implantable medical device. More specifically, the invention relates to an implantable pulse generator (IPG) for a medical device, the IPG having the ability to sense the presence of an external magnetic field, such as a magnetic field associated with magnetic resonance imaging, and to take appropriate actions to protect the patient and the IPG.

BACKGROUND

Implantable stimulation devices are devices that generate and deliver electrical stimuli to body nerves and tissues for the therapy of various biological disorders, such as pacemakers to treat cardiac arrhythmia, defibrillators to treat cardiac fibrillation, cochlear stimulators to treat deafness, retinal stimulators to treat blindness, muscle stimulators to produce coordinated limb movement, spinal cord stimulators to treat chronic pain, cortical and deep brain stimulators to treat motor and psychological disorders, and other neural stimulators to treat urinary incontinence, sleep apnea, shoulder subluxation, etc. FIG. 1 shows an implantable stimulation device 1 as may be used for spinal cord stimulation or deep brain stimulation. Such a device 1 typically includes an Implantable Pulse Generator (IPG) 10, which includes a biocompatible device case 12 formed of a conductive material such as titanium for example. The case 12 typically holds the circuitry and battery necessary for the IPG 10 to function, although IPGs can also be powered via external RF energy and without a battery. The IPG 10 is coupled to electrodes 16 via one or more electrode leads 18, such that the electrodes 16 form an electrode array 20. The electrodes 16 are carried on a flexible body which also houses the individual signal wires 24 coupled to each electrode. In the illustrated embodiment, there are eight electrodes on each lead 18, although the number of leads and electrodes is application specific and therefore can vary. The leads 18 couple to the IPG 10 using lead connectors 26, which are fixed in a non-conductive header material 28, which can comprise an epoxy for example.

FIG. 2 shows a first embodiment 201 of implantable stimulation device implanted in a patient for deep brain stimulation and a second embodiment 202 implanted in the patient for spinal cord stimulation. For deep brain stimulation, the IPG 10 is typically embedded in the in the patient's chest inferior to the clavicle. The signal wires 24 are routed beneath the skin of the patient's neck and head and the leads 18 are implanted into the patient's brain 32. For spinal cord stimulation, the IPG 10 is typically embedded in the in the patient's buttock and the leads 18 are implanted into the patient's spinal column.

The implantable stimulation device may further comprise a handheld Remote Control (RC) (not shown) to remotely instruct the neurostimulator to generate electrical stimulation pulses in accordance with selected stimulation parameters. The RC is used to send data to and receive data from the IPG 10. For example, the RC can send programming data to the IPG 10 to dictate the therapy the IPG 10 will provide to the patient. Also, the RC can act as a receiver of data from the IPG 10, such as various data reporting on the IPG's status. Wireless data transfer between the IPG 10 and the RC can take place via magnetic inductive coupling. To implement such functionality, both the IPG 10 and the RC typically have electrical coils that can act as the transmitter or the receiver, thus allowing for two-way communication between the two devices, as is well known in the art.

IPGs are routinely implanted in patients who are in need of Magnetic Resonance Imaging (MRI). Thus, when designing implantable neurostimulation systems, consideration must be given to the possibility that the patient in which neurostimulator is implanted may be subjected to electromagnetic forces generated by MRI scanners, which may potentially cause damage to the neurostimulator as well as discomfort to the patient. In particular, in MRI, spatial encoding relies on successively applying magnetic field gradients. The magnetic field strength is a function of position and time with the application of gradient fields throughout the imaging process. Gradient fields typically switch gradient coils (or magnets) ON and OFF thousands of times in the acquisition of a single image in the present of a large static magnetic field. Present-day MM scanners can have maximum gradient strengths of 100 mT/m and much faster switching times (slew rates) of 150 mT/m/ms, which is comparable to stimulation therapy frequencies. Typical MRI scanners create gradient fields in the range of 100 Hz to 30 KHz, and radio frequency (RF) fields of 64 MHz for a 1.5 Tesla scanner and 128 MHz for a 3 Tesla scanner.

The strength of the gradient magnetic field may be high enough to induce voltages (5-10 Volts depending on the orientation of the lead inside the body with respect to the MRI scanner) on to the stimulation lead(s) 18, which in turn, are seen by the IPG electronics. If these induced voltages are higher than the voltage supply rails of the IPG electronics, there could exist paths within the IPG that could induce current through the electrodes on the stimulation lead(s), which in turn, could cause unwanted stimulation to the patient due to the similar frequency band, between the MM-generated gradient field and intended stimulation energy frequencies for therapy, as well as potentially damaging the electronics within the IPG. The gradient (magnetic) field may induce electrical energy within the wires of the stimulation lead(s), which may be conveyed into the circuitry of the IPG and then out to the electrodes of the stimulation leads.

Accordingly, the IPG may feature an MM-safe mode that protects the IPG 10 and the patient from damage or injury due to magnetic field-induced electrical energy when the patient undergoes an MRI. For example, in MRI-safe mode, the IPG may cease providing stimulation to the patient. Additionally, (or alternatively) the IPG may increase the voltage within the IPG to prevent unwanted induced current through the IPG. The IPG may modify or suspend other operations, such as passive charge recovery, an operation whereby charge is passively conveyed to AC ground by closing switches associated with the active electrodes. Within an MRI, the closed switches may potentially provide a path for magnetically induced currents into and out of the IPG. The recovery switches are therefore left open during MRI-safe mode.

The IPG can be set to MM-safe mode using the RC. Additionally, some IPGs can be set to MM mode by placing a magnet against the patient's skin over the IPG. Some IPGs include internal magnetic sensors, typically Hall effect magnetic sensors, that are capable of sensing an external magnetic field, such as an MM field. Hall effect magnetic sensor have a limitation in that they are unidirectional. In other words, a Hall effect magnetic sensor is only effective when it is situated in a particular orientation with respect to the magnetic field. Therefore, a series of three orthogonally oriented Hall effect sensors must be used to reliably sense the presence of an external magnetic field. Such a sensor design is undesirably large.

DESCRIPTION

Figure 1:
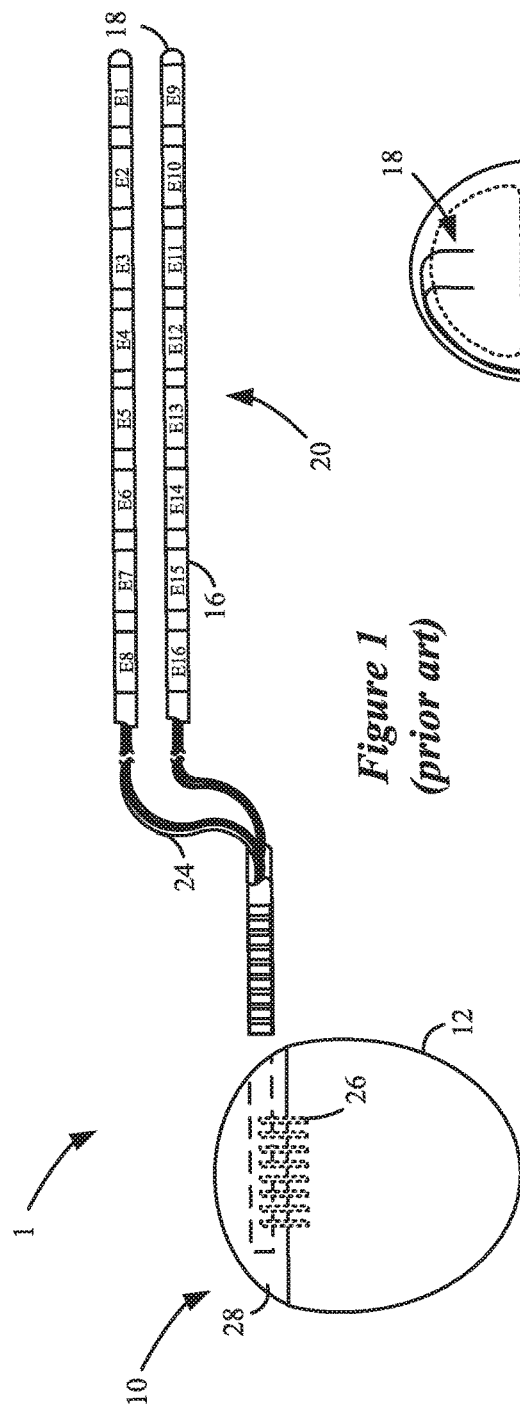
FIG. 1 shows a medical device including an IPG.
Figure 2:
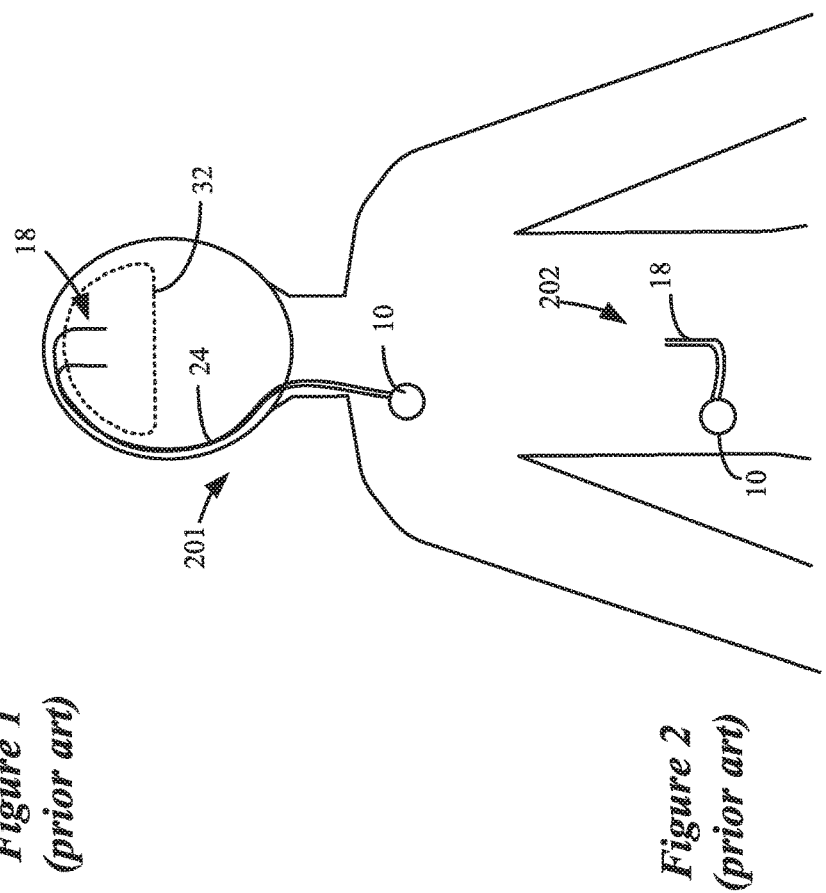
FIG. 2 shows an embodiments of a medical devices implemented for DBS and for SCS.
Figure 3:
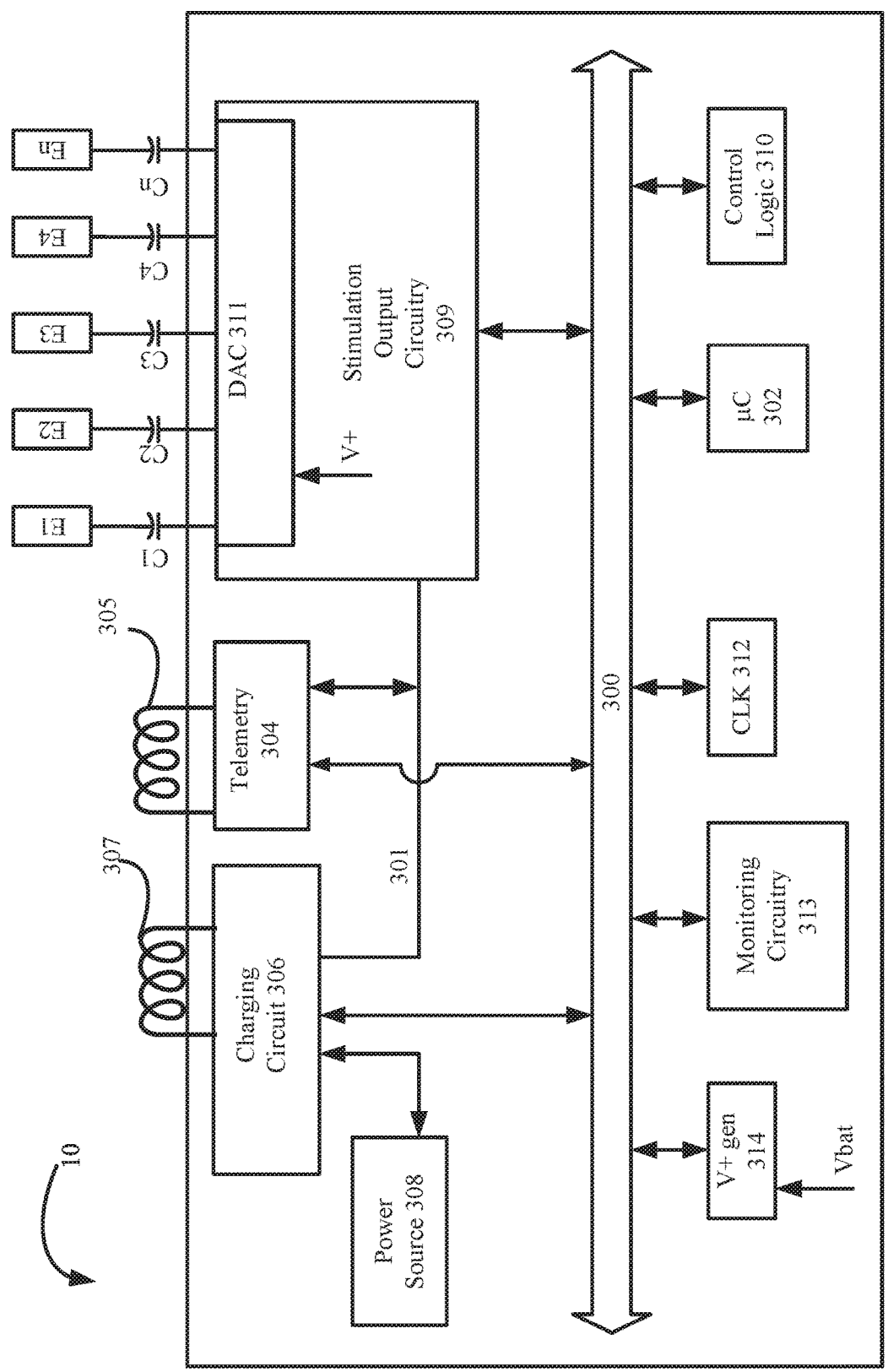
FIG. 3 shows various components of an IPG.

FIG. 3 illustrates the internal components (represented as blocks) of an IPG 10 that are relevant in this disclosure. Note that IPG 10 includes many other components that are not discussed. Each of the blocks represent circuits or groups of circuits that perform standard functions within the IPG 10.

Communication among internal components within the IPG 10 may be via one or more digital busses 300 and analog busses 301. The microcontroller (μC, 302) functions as the master controller for all of the other blocks. The telemetry block 303 couples to a telemetry coil 304 and includes transceiver circuitry for communicating with an external controller. The charging block 306 couples to a charging coil 307 and includes charging circuitry for rectifying power received from an external charger and for charging the power source (battery, 308) in a controlled fashion.

The microcontroller 302 is coupled to monitoring circuitry 313, which monitors the status of various nodes or other points throughout the IPG 10. For example, the monitoring circuitry can monitor power supply voltages, current values, temperature and impedances of the electrodes E1-En. As discussed in more detail below, the monitoring circuitry can monitor voltages across components of the stimulation output circuitry 309.

The stimulation output circuitry 309 includes circuitry for generating electrical stimulation energy in accordance with a defined pulsed waveform having a specified pulse amplitude, pulse rate, pulse width, pulse shape, and burst rate under control of control logic 310. The stimulation output circuitry 309 is coupled to the electrodes E1-En and includes drivers for the electrodes, with a digital-to-analog converter (DAC) 311 being responsive to the stimulation program to supply the specified electrode currents. The electrodes E1-En are coupled to capacitors C1-Cn, which prevent injection of DC current into the patient's tissue. Clock circuitry 312 and V+ generation circuitry 314 will be discussed in more detail below. For now, merely note that V+ generation circuitry provides a high voltage, V+ (referred to as compliance voltage, typically on the order of about 15 V) by boosting the voltage provided by the power source 308 (referred to as Vbat, typically about 3 V). For reasons explained below, DAC 311 requires a high voltage source V+ to operate properly.

Figure 4:
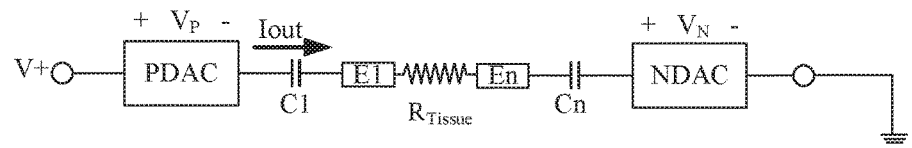
FIG. 4 illustrates an electrical stimulation path through a patient's tissue.

FIG. 4 illustrates a circuit 400 through which stimulation current $I_{out}$ flows when stimulating a patient using electrodes E1 and En. The resistance of the patient's tissue is represented by a resistor $R_{Tissue}$. In the illustrated circuit 400, electrode E1 is an anode, i.e., a current source, and electrode En is a cathode, i.e., a current sink. The magnitude of current, $I_{out}$, and the amount of time it is applied (the pulse width) is prescribed by the therapy that the patient is to receive. The DAC circuitry 311 sets the current $I_{out}$ based on digital control signals, for example, from control logic circuitry 310 (see FIG. 3). DAC circuitry that sources anodic current is referred to as a PDAC; DAC circuitry that sinks cathodic current is referred to as an NDAC. The compliance voltage V+ provides the driving force for $I_{out}$. Each element of circuit 400 drops some portion of compliance voltage V+. The voltage drops can be denoted as follows: $V_P$ is the voltage drop across the PDAC, Vc1 drops across the capacitor C1, $V_R$ drops across the resistance due to the patient's tissue, Vc3 drops across the capacitor Cn, and $V_N$ drops across the NDAC. The total voltage drop is $V+=V_P+VC1+V_R+Vcn+V_N$. The voltage drop through the tissue, $V_R$, is difficult to know a priori, but in any event will remaining constant over the duration of a current pulse. By contrast, the voltage drops across the decoupling capacitors, Vc1 and Vc2, will increase as current is injected through them the capacitors.

If V+ is set to a constant value, the voltage drops across the PDAC and NDAC (i.e., $V_P$ and $V_N$, respectively) will necessarily decrease because Vc1 and Vc2 increase. The changing voltage drops of the PDAC and NDAC can cause problems because those elements contain output transistors that operate at optimal voltages. The optimal voltage for the PDAC $V_P$ (opt) is typically about 1.5V and the optimal voltage for the NDAC $V_N$ (opt) is typically about 1.2V. (The difference between the values of $V_P$ (opt) and $V_N$ (opt) is because the PDAC uses p-channel transistors and the NDAC uses n-channel transistors). When the PDAC and/or NDAC operate below the optimal voltage, they are not able to provide the desired current. Operating above the optimal voltage wastes power and generates unnecessary heat. It is therefore desirable to operate the PDAC and the NDAC at or just slightly above the optimal voltages. The compliance voltage V+ often needs to be adjusted to a proper value for allowing the PDAC and NDAC to operate at their optimal values.

Figure 5:
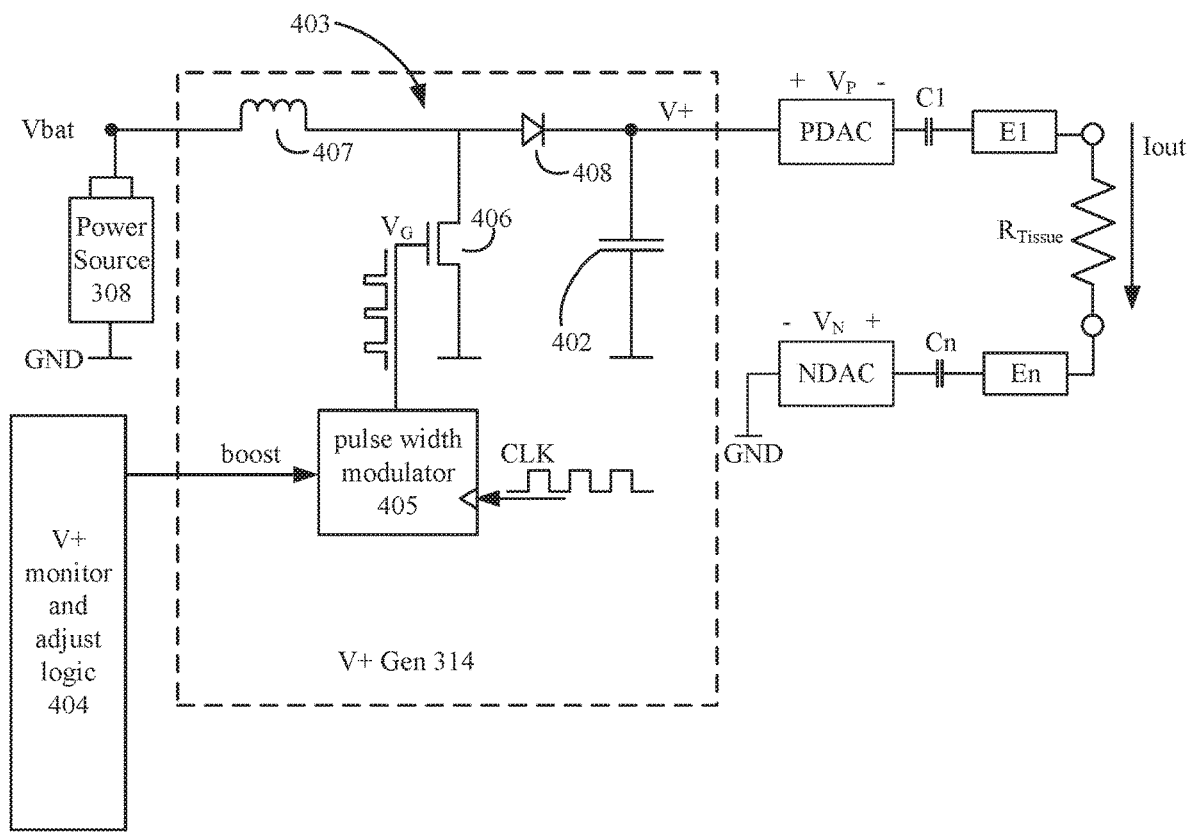
FIG. 5 illustrates a boost circuit for providing a compliance voltage.

FIG. 5 illustrates aspects of the V+ generation circuitry 314 that provides V+. The V+ generation circuitry includes a boost converter circuit 403 that provide that comprises a capacitor 402, an inductor 407, a transistor 406 and a diode 408. The power source 308 provides a voltage Vbat to the boost converter circuit 403. When the transistor 406 is on, current flows through the inductor 407 to ground. When the transistor 406 is off current in the inductor 407 discharges through the diode 408 to the charging capacitor 402. The charge building on the charging capacitor is the compliance voltage V+. The turning on and off of the inductor is controlled by its gate voltage, $V_G$, which is an oscillating clock signal CLK modulated by a pulse width modulator 405.

V+ monitor and adjust logic circuitry 404 (which may comprise part of the IPG's microcontroller 302 or the IPG's monitoring circuitry 313, or may be a standalone circuit block) adjusts V+ so that the DACs operate at optimum voltages. Details about how the V+ monitor and adjust logic circuitry 404 works are well described in the prior art, and are not described here in detail. See, for example, U.S. Pat. No. 8,175,719, issued May 8, 2012; U.S. Pat. No. 9,174,051, issued Nov. 3, 2015; and U.S. Pat. No. 9,314,632, issued Apr. 19, 2016, the entire contents of each being incorporated herein by reference. Briefly, the V+ monitor and adjust logic circuitry 404 includes voltage sensing circuitry that senses the voltages $V_P$ and $V_N$ at the PDAC and NDAC. If $V_P$ and/or $V_N$ falls below an optimum operating value, the V+ monitor and adjust logic circuitry executes an algorithm to determine an amount to increase V+ and outputs an appropriate "boost" signal to the pulse width modulator 405.

The boost signal instructs the pulse width modulator 405 how to adjust the pulse width of a clock signal, CLK, thereby determining how $V_G$ is modulated. How the pulse width modulator 405 modulates $V_G$ determines the percentage of time the transistor 406 is turned on, referred to as the transistor's duty cycle. The V+ monitor and adjust logic circuitry increases the duty cycle of the transistor 406 to increase V+ and decreases the duty cycle to decrease V+. The reason for this is explained in more detail below.

Figure 6:
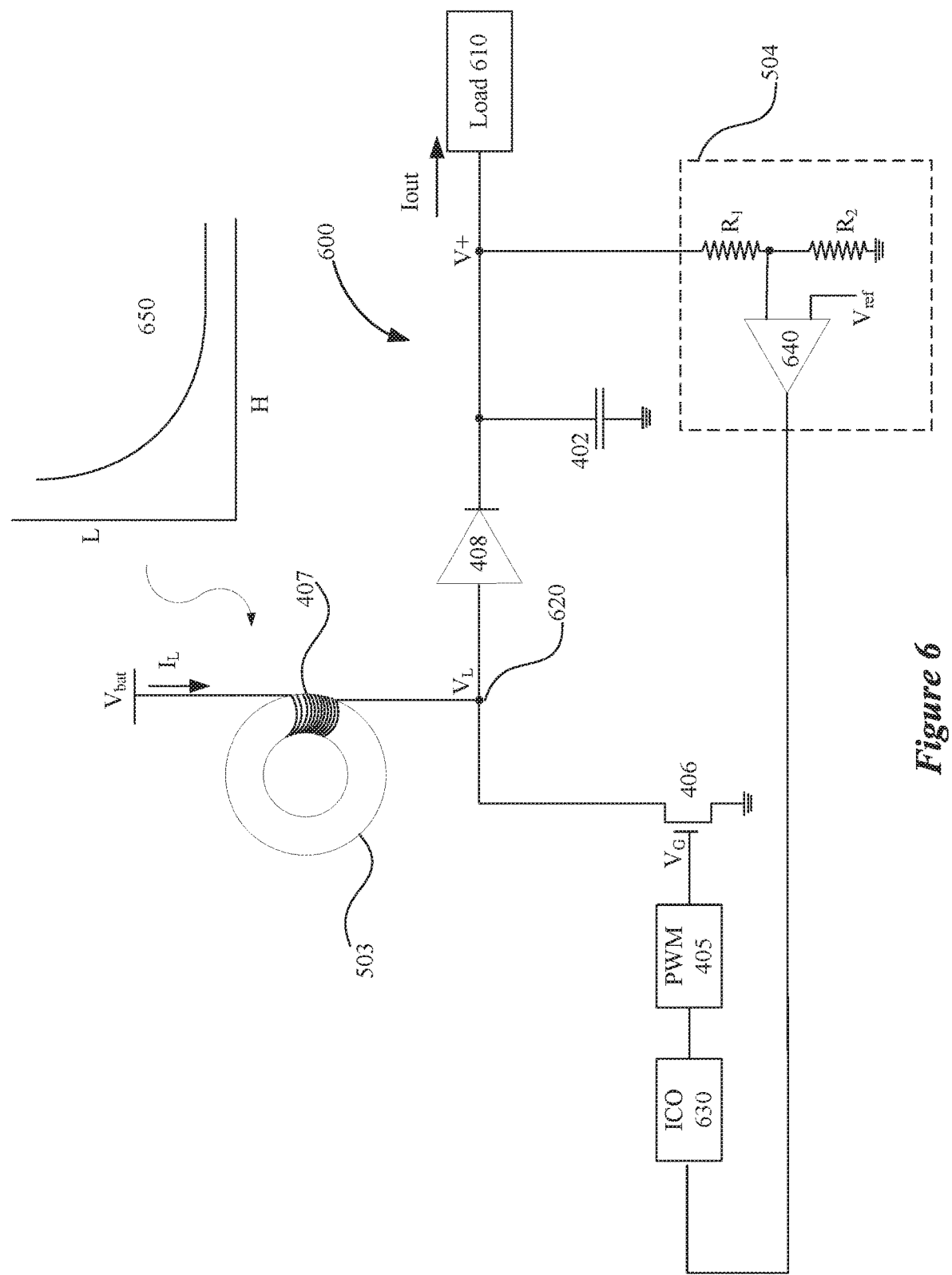
FIG. 6 shows a circuit for detecting an external magnetic field.

The inventors have discovered that a boost converter circuit, such as the one illustrated in FIG. 5, can be used to detect and monitor the presence of a magnetic field, such as a magnetic field associated with an MRI. FIG. 6 is a simplified illustration of a boost converter circuit 600 and aspects of related logic useful for illustrating how the circuit can be used to detect the presence of a magnetic field. As with the boost converter circuit 403 of FIG. 5, circuit 600 of FIG. 6 includes a capacitor 402, an inductor 407, a transistor 406 and a diode 408. The inductor 407 includes a ferrite core provided by a section of a toroidal ferrite magnet 503. While a toroidal magnet is shown in FIG. 6, other geometries can be used. In circuit 600, a current $I_{out}$ is provided to a generic load 610, which can be thought of as the circuit through the DACs, coupling capacitors, and tissue resistance, illustrated in FIG. 5.

Figure 7:
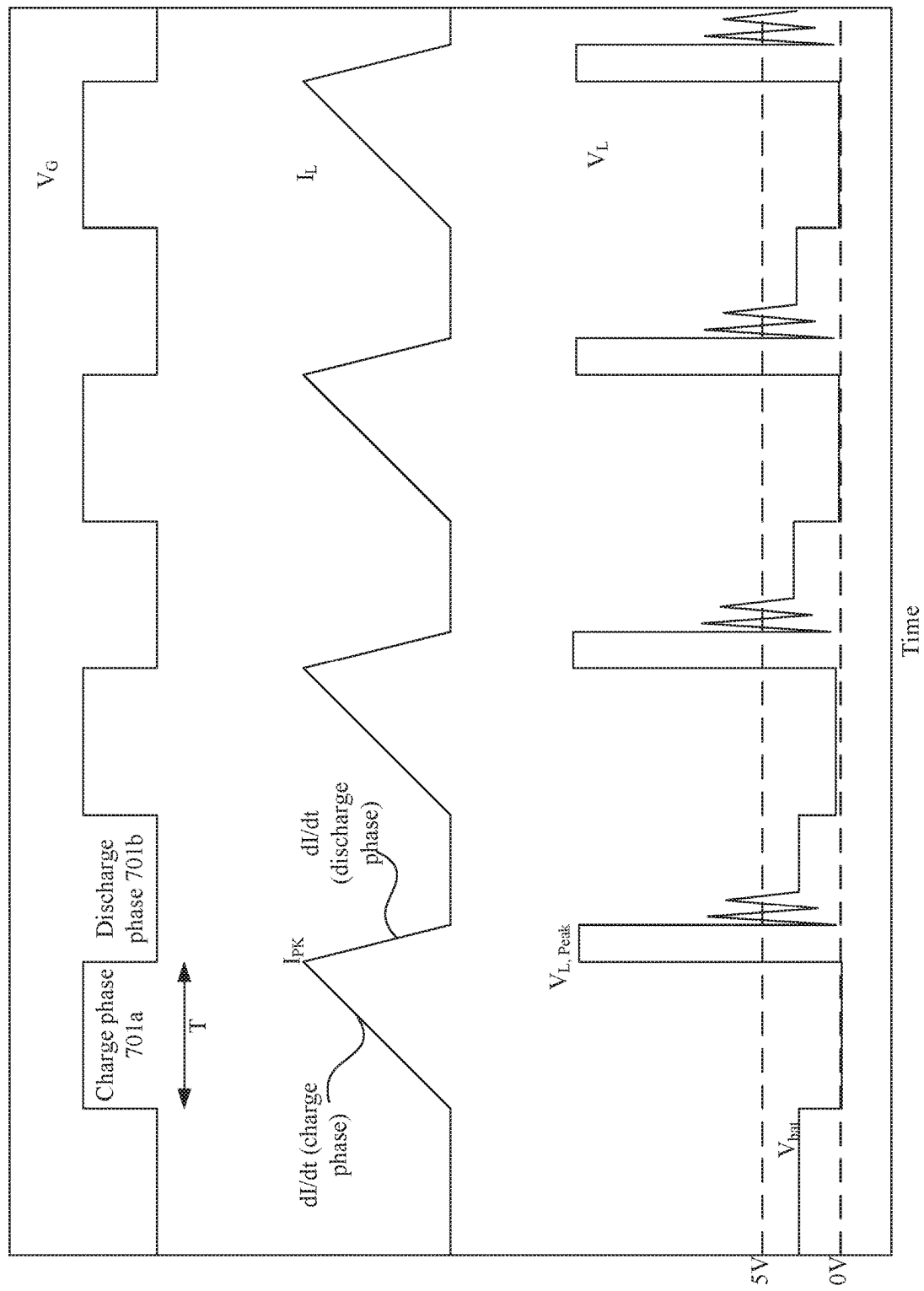
FIG. 7 shows inductor current and voltage behavior for the circuit illustrated in FIG. 6.

As explained above, when the transistor 406 is on, current flows through the inductor 407 to ground. When the transistor 406 is off current in the inductor 407 discharges through the diode 408 to the charging capacitor 402. FIG. 7 illustrates the current IL through the inductor and the voltage $V_L$ at node 620 as a function of the oscillating gate voltage $V_G$. The top line shows $V_G$. The charge phase 701a is the time that the transistor 406 is turned on and current is flowing through the inductor 407 to ground. The discharge phase 701b is when the transistor 406 is turned off and charge stored in the inductor 407 can flow through diode 408.

The middle line IL represents the current across the inductor 407. During the charge phase the inductor current rises linearly to a peak current $I_{PK}$, according to Eq. 1:

$$\frac{dI}{dt} = \frac{V_{bat}}{L} \qquad \text{Eq. 1}$$

where L is the inductance of the inductor 407. The peak current $I_{PK}$ can be calculated by Eq. 2:

$$I_{PK} = \frac{V_{bat}T}{L} \qquad \text{Eq. 2}$$

where T is time of a single charge phase.

Assume that the transistor is turning on and off such that period for a single on-off cycle is P and that the percentage of time that the transistor is on during a single cycle is D (the duty cycle). Then T=DP. Since the frequency f is 1/P, the formula for the peak current $I_{PK}$ can be rewritten in terms of frequency and duty cycle as shown in Eq. 3:

$$I_{PK} = \frac{V_{bat}D}{2Lf} \qquad \text{Eq. 3}$$

As the current flows through the inductor 407, energy is stored in the inductor's magnetic field. That energy is described by Eq. 4:

$$E = \tfrac{1}{2} L I_{PK}^2 \qquad \text{Eq. 4}$$

When the transistor 406 is turned off at the beginning of the discharge phase, the current through the inductor 407 rapidly drops, producing a back e.m.f. in the inductor 407. The energy stored in the inductor 407 is discharged through the diode 408 and the voltage $V_L$ at node 620 swings high to a peak voltage $V_{L,\, Peak}$. Current flows through the diode 408 to the capacitor 409 during the discharge phase if $V_L$ is greater than V+. As shown in the energy equation, the amount of energy transferred increases as the square of the peak current $I_{PK}$. Moreover, $I_{PK}$ increases as a function of the duty cycle D. Thus, increasing the duty cycle D increases the current discharged through the diode 408, thereby increasing the compliance voltage V+.

Recall from the discussion of FIG. 5, that the V+ monitor and adjust logic circuitry 404 executes an algorithm based on the voltages $V_P$ and $V_N$ of the DACS to determine if the compliance voltage V+ should be adjusted and then provides an appropriate boost signal to adjust the duty cycle of the transistor 406 accordingly. That aspect of the V+ monitor and adjust logic circuitry 404 is illustrated in FIG. 6 as a comparator circuit 504 and a current controlled oscillator 630. The comparator circuit includes a comparator 640 that is configured to compare the value of V+ (adjusted by a voltage divider circuit comprising R1 and R2) with a reference voltage $V_{ref}$. The value of $V_{ref}$ is programmed algorithmically based on measurements of $V_P$ and $V_N$. If the divided V+ falls below the programmed value of $V_{ref}$, the comparator 640 sends an output to the current controlled oscillator and pulse width modulator 405 that increases the duty cycle of the voltage signal provided to the gate of the transistor 406, thereby increasing V+. When the adjusted value of V+ exceeds $V_{ref}$, the comparator sends a signal that decreases the duty cycle of the voltage signal provided to the gate of the transistor 406.

In the absence of an external magnetic field, the inductance of the inductor 407 remains constant. However, when it is subject to a strong magnetic field, the magnet 503 at the core of the inductor "saturates," meaning that it becomes less able to support magnetic field generated by charges moving within the wire coil of the inductor. As a result, the inductance of the inductor 407 decreases in the presence of an external magnetic field. The inductance drops by about two orders of magnitude in a 1.5 tesla external magnetic field, such that the inductor 407 behaves essentially like an air-core inductor. Curve 650 of FIG. 6 illustrates the drop in inductance as a function of magnetic field, H.

Figure 8:
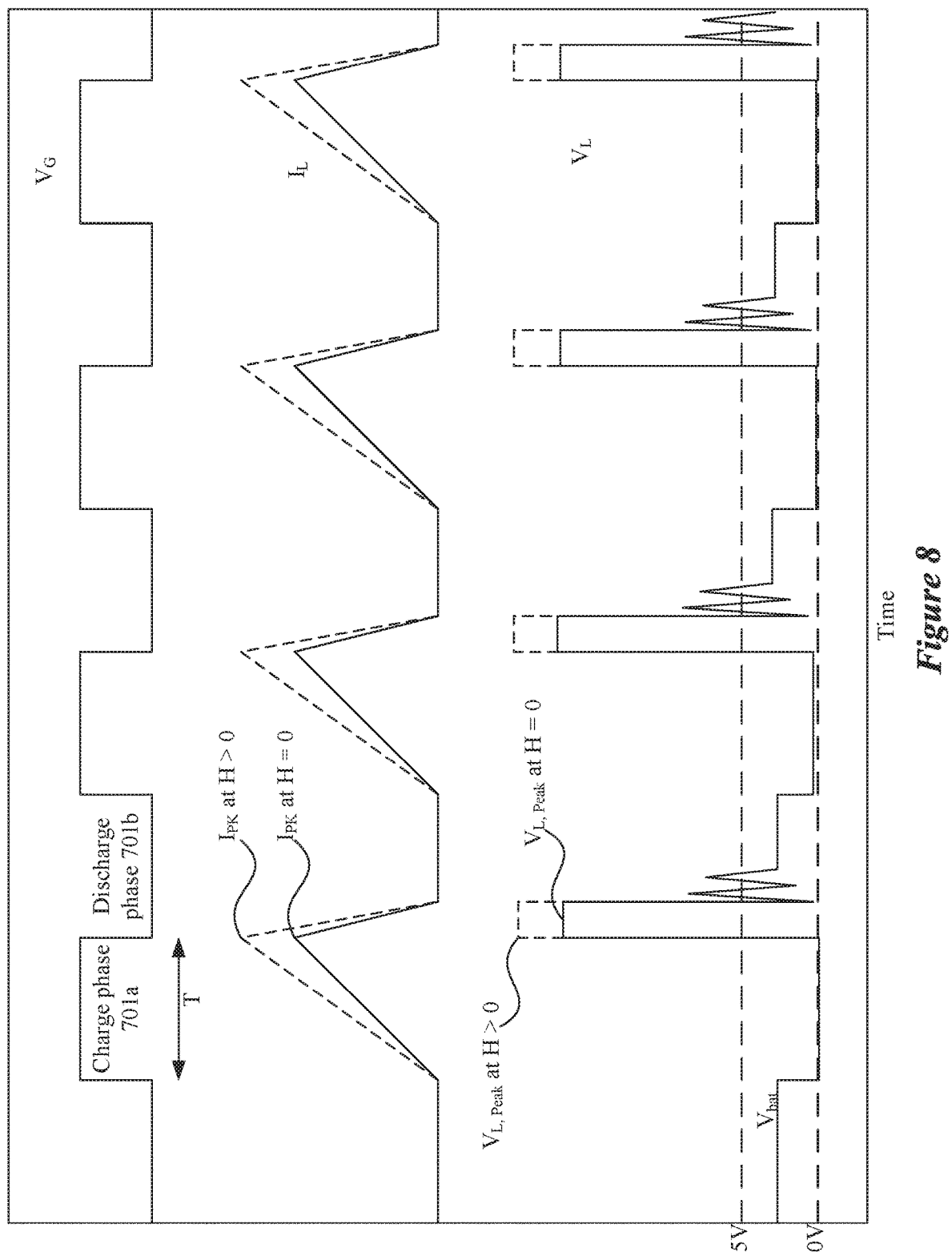
FIG. 8 shows inductor current and voltage behavior for the circuit illustrated in FIG. 6 in the presence and absence of an external magnetic field.

From equations Eq. 1-Eq. 3, it is apparent that when the inductance L of the inductor 407 decreases due to saturation, dI/dt and $I_{PK}$ increase. Consequently, the magnitude of the spike in voltage $V_{L,Peak}$ at node 620 also increases. The dashed lines in FIG. 8 show the changes in $I_{PK}$ and $V_{L,Peak}$ when the inductance L of the inductor 407 decreases due to saturation.

The increase in the magnitude of $V_{L,Peak}$ as a consequence of the inductor core becoming saturated can be used to detect when the IPG is in a magnetic field. Moreover, when $V_L$ increases V+ also increases. Referring to FIG. 6, the relationship between the inductance L of the inductor 407, the output current $I_{out}$, the compliance voltage V+, the battery voltage $V_{bat}$, the frequency f and duty cycle D of gate voltage $V_G$ is defined by the duty cycle equation, Eq. 5:

$$D = \sqrt{\frac{(V+) - V_{bat}}{V_{bat}^2} 2I_{Out} fL} \qquad \text{Eq. 5}$$

Each of the variables of Eq. 5 are very precisely known in the IPG—$V_{bat}$ and $I_{out}$ are monitored using monitoring circuitry 313 (FIG. 3); f is the frequency of the current controlled oscillator 630; D is the duty cycle of the pulse width modulator 405; and V+ is set by the V+ monitor and adjust logic circuitry and can also be independently measured using the monitoring circuitry 313. Finally, L is the inductance of the inductor 407 and is known (in the absence of an external magnetic field) because the inductor is chosen by design.

However, when the IPG is within an external magnetic field that is strong enough to begin saturating the core of the inductor 407, the measured V+ will not agree with the value calculated according to Eq. 5 using the known values for the variables. Instead, the measured V+ will exceed the expected value because the inductance L will be less than expected.

According to some embodiments, the IPG periodically measures V+. For example, the IPG may use the monitoring circuitry 313 to measure V+ every second or multiple times per second, such as three times per second. If the monitoring circuitry senses a sudden increase in V+, then the IPG can be instructed to activate its MRI-safe mode. According to some embodiments, the monitoring circuitry may compare the increase in V+ to threshold value (3 V, for example) and set the IPG to MM-safe mode only if the increase exceeds that threshold value.

As mentioned above, entering MRI-safe mode may cause the IPG to take one or more actions, such as: (1) ceasing to provide stimulation to the patient, (2) increasing the compliance voltage V+ to prevent unwanted induced current through the IPG, (3) confirming that the battery is fully charged, (4) suspending passive charge recovery.

Figure 9:
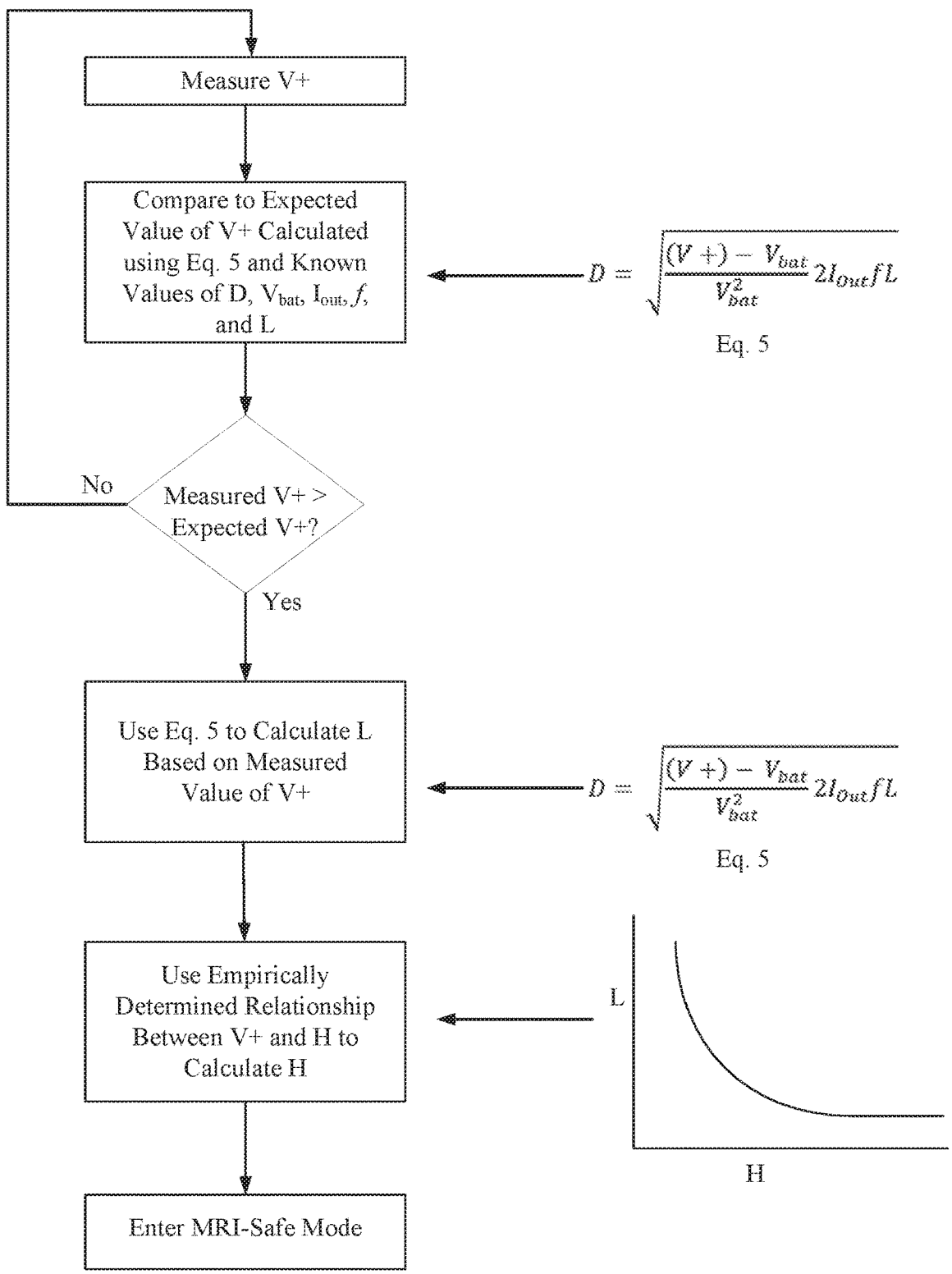
FIG. 9 shows a process for measuring an external magnetic field.

FIG. 9 illustrates an alternative process for determining the presence of an external magnetic field based on saturation the inductor magnet. Periodically during operation, the IPG's monitoring circuitry 313 measures V+ and compares the measured V+ to an expected value of V+ that is calculated using the duty cycle equation (Eq. 5) based on measured values of $V_{bat}$ and $I_{out}$, set values of f and D, and the nominal value of L. If the measured value of V+ is greater than the expected value, then the IPG executes an algorithm that uses Eq. 5 to calculate the true inductance L based on the measured value of V+ and the other known variables.

Figure 11:
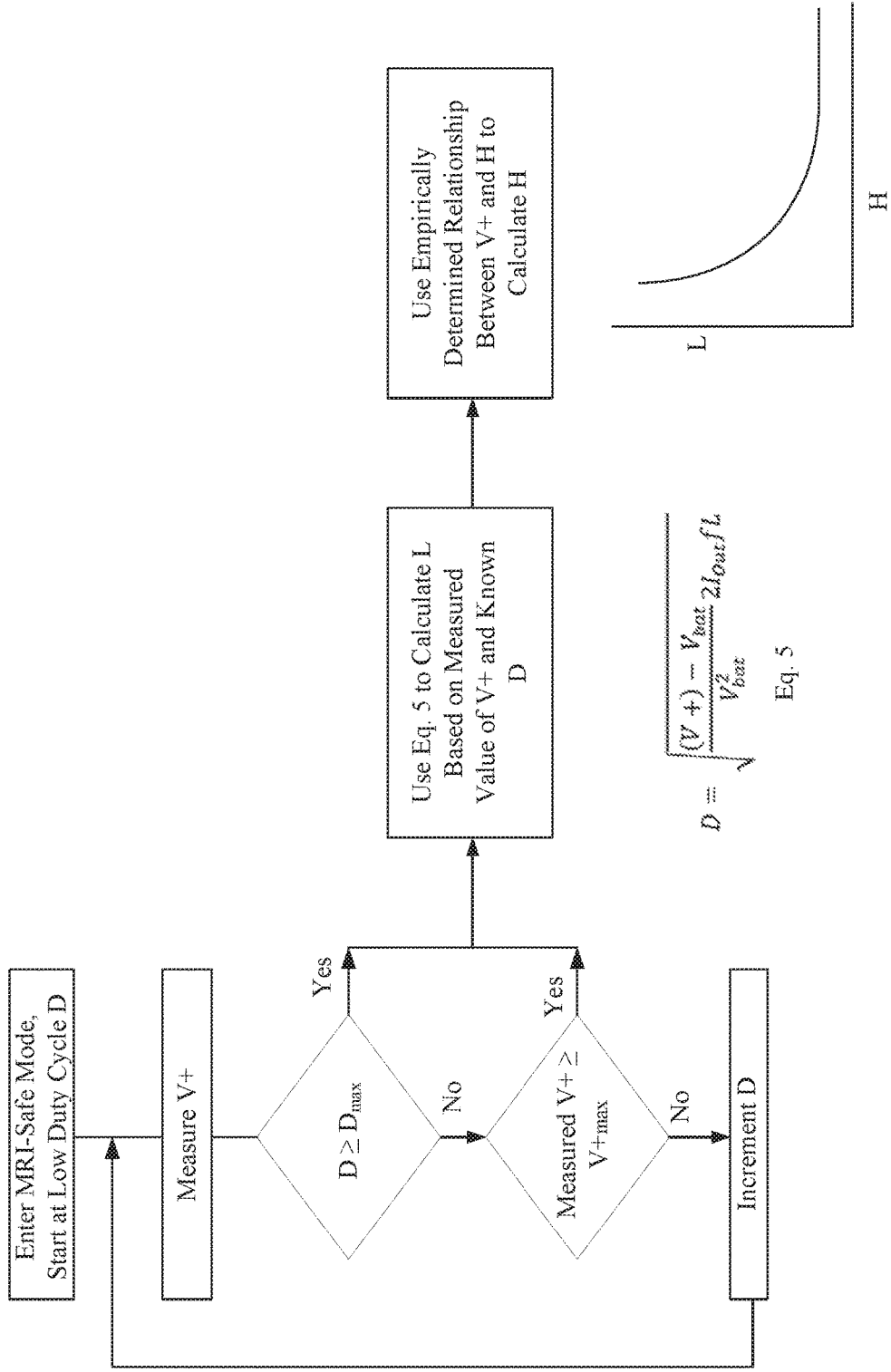
FIG. 11 shows a method for adjusting the duty cycle of a compliance voltage circuit when an IPG detects an external magnetic field.

If the calculated inductance is less than the nominal inductance (i.e., the inductance rating of the inductor used in the circuit), then it is assumed that the inductor is at least partially saturated due to the presence of an external magnetic field. According to some embodiments, the IPG can calculate the strength of the external magnetic field based on a function relating the inductance to magnetic field strength. Such a function would have to have been calculated empirically beforehand and programmed into the IPG. FIG. 11 illustrates inductance v. magnetic field relationships calculated empirically for two inductors.

The IPG can take steps to enter MM-safe mode if the calculated magnetic field exceeds a threshold value. In alternative embodiments wherein the IPG is not programmed to calculate the strength of the magnetic field, the IPG can take steps to enter an MM-safe mode based on the calculated decrease in inductance. Moreover, the IPG can take steps to enter an MM-safe mode based on an increase in V+, as mentioned above.

According to a further embodiment, the IPG is already in an MM-safe mode and executes an algorithm to adjust the duty cycle of the pulse width modulator 405 (FIG. 6) based on the strength of an external magnetic field. Recall that in MM-safe mode, the IPG sets the compliance voltage V+ to a high level to prevent unwanted induced current through the IPG. Referring to FIG. 6, the IPG would generally increase the duty cycle of the pulse width modulator 405, for example by increasing the value of Vref in the comparator circuit 504, in order to drive the compliance voltage V+ to the high value needed in MM-safe mode. But if the inductance of the inductor 407 drops significantly due to saturation by the external magnetic field, a higher than expected current will run through the transistor 406 when the transistor is on. If the duty cycle is too great (i.e., the transistor is on for too much of the time), then so much current may flow through the transistor that it fails, a condition known as runaway.

Figure 10:
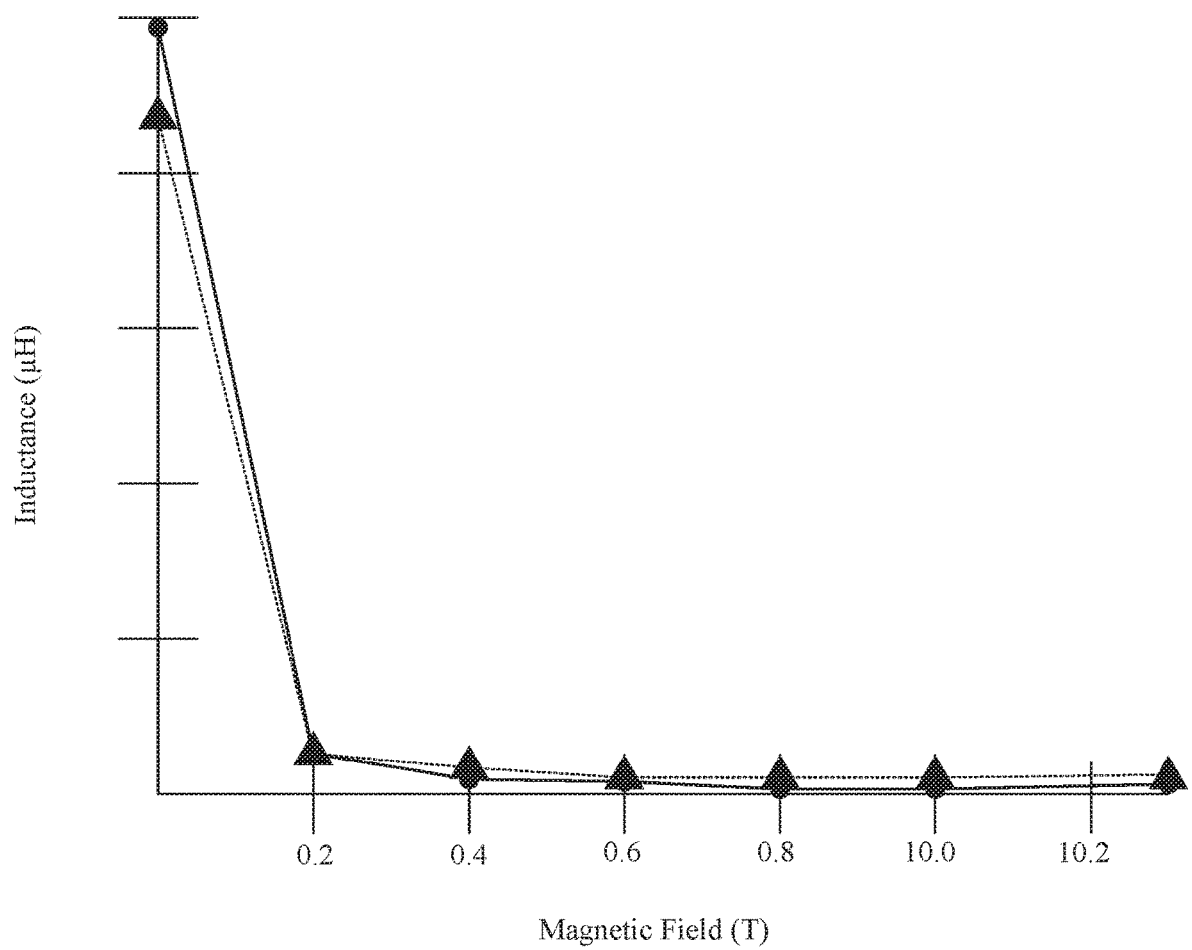
FIG. 10 shows the relationship between inductance and external magnetic field for two sample inductors.

FIG. 10 illustrates a process for moderating the duty cycle of the pulse width modulator 405 (and thereby the time transistor 406 is on) so as to prevent runaway while setting an adequate compliance voltage V+ in MRI-safe mode. The process begins when the IPG is in MRI-safe mode. Rather than immediately increasing the duty cycle to drive V+ high, the duty cycle is set low and the IPG's monitoring circuitry 313 measures V+. The IPG determines if the target V+ value has been reached and also determines if the pulse width modulator 405 is providing a duty cycle that is greater than or equal to the maximum duty cycle $D_{max}$. $D_{max}$ is generally a design constraint of the particular IPG implementation and is determined based on factors that are not relevant here. For present purposes, it need only be appreciated that $D_{max}$, if it exists, is a constraint built into the IPG system.

If neither the $D_{max}$ or $V+_{max}$ conditions are met, then the IPG incrementally increases the duty cycle and re-executes the measurement and determinations at the new increased duty cycle. If either $V+_{max}$ or $D_{max}$ are met, then the IPG ceases incrementing D. The IPG then can calculate the inductance L using Eq. 5. According to some embodiments, the IPG can calculate the magnetic field strength H, from empirically derived data as described above.

It should be noted here that the circuit described herein and used for induction-based determination of an external magnetic field is a boost circuit that is commonly used to provide a compliance voltage in an IPG. Extending the boost circuit for magnetic field detection offers advantages in space saving and design considerations, especially compared to using Hall effect transistors. However, it should be appreciated that a circuit, similar to the one illustrated in FIG. 6, can be implemented as a "stand-alone" sensor for magnetic field detection. In other words, it is not required that the same circuit be used for both compliance voltage and magnetic field detection.

Although particular embodiments of the present invention have been shown and described, it should be understood that the above discussion is not intended to limit the present invention to these embodiments. It will be obvious to those skilled in the art that various changes and modifications may be made without departing from the spirit and scope of the present invention. Thus, the present invention is intended to cover equivalents that may fall within the spirit and scope of the present invention as defined by the claims.

What is claimed is:

1. An implantable pulse generator (IPG) configured to provide therapy to a patient, the IPG comprising:
    first circuitry configured to boost a first voltage to a second voltage, the first circuitry comprising a magnetic-core inductor having an inductance, and
    second circuitry configured to detect a change in the second voltage, the change in the second voltage indicating a change in the inductance when the IPG is in the presence of an external magnetic field, wherein
    the first circuitry is a boost converter circuit configured to provide a compliance voltage and wherein the second voltage is the compliance voltage.

2. The IPG of claim 1, wherein the first circuitry further comprises:
    a transistor configured to receive a gate voltage, the gate voltage having an oscillation frequency and being modulated by a pulse width modulator having a duty cycle, and
    an output stage configured to use the second voltage to drive a known current through a load, wherein detecting a change in the second voltage comprises:
    calculating an expected second voltage value from known values of the current, the first voltage, the oscillation frequency, and the duty cycle, and an assumed value for the inductance,
    measuring the second voltage, and
    comparing the second voltage to the calculated expected second voltage.

3. The IPG of claim 2, wherein detecting a change in the second voltage further comprises calculating the inductance based on the measured second voltage.

4. The IPG of claim 3, further comprising a processor configured to determine an external magnetic field strength based on the calculated inductance.

5. The IPG of claim 1, wherein the IPG is configured to change from a first operational mode to a second operational mode based on the detected change in the parameter of the first circuitry second voltage.

6. The IPG of claim 5, wherein the first operational mode is a normal mode and the second operational mode is an MRI-safe mode.

7. The IPG of claim 6, wherein the MM-safe mode comprises disabling the IPG from providing stimulation to the patient.

8. The IPG of claim 6, wherein the MM-safe mode comprises increasing a compliance voltage.

9. The IPG of claim 6, wherein the MM-safe mode comprises disabling passive charge recovery.

10. The IPG of claim 1, wherein the first circuitry further comprises:
    at least one diode,
    at least one capacitor, and
    at least one transistor configured to receive a gate voltage, the gate voltage having an oscillation frequency and being modulated by a pulse width modulator having a duty cycle, wherein
    the first circuitry is configured so that when the at least one transistor is on, the inductor discharges to ground, and when the at least one transistor is off, the inductor discharges through the at least one diode to the at least one capacitor.

11. The IPG of claim 10, wherein the duty cycle is adjustable to maintain the second voltage on the at least one capacitor.

12. The IPG of claim 11, wherein the first circuitry is configured to use the second voltage to drive a known current through a load.

13. The IPG of claim 12, wherein the load comprises digital-to-analog (DAC) circuitry configured to supply current to one or more electrodes.

14. The IPG of claim 11, wherein detecting the change in the second voltage comprises:
    calculating an expected second voltage value from known values of the current, the first voltage, the oscillation frequency, and the duty cycle, and an assumed value for the inductance,
    measuring the second voltage, and
    comparing the second voltage to the calculated expected second voltage.

15. The IPG of claim 14, wherein the second circuitry comprises a comparator circuit configured to compare the second voltage to a reference voltage.

16. The IPG of claim 1, wherein the magnetic-core inductor comprises a toroidal magnet.

* * * * *